(12) United States Patent
Ikada et al.

(10) Patent No.: US 6,391,055 B1
(45) Date of Patent: *May 21, 2002

(54) ARTIFICIAL CORNEA

(75) Inventors: Yoshito Ikada, Uji; Junichi Ohashi, Kasugai; Naoki Kondo, Kasugai; Aoi Nishizawa, Kasugai; Ichiro Ando, Kasugai, all of (JP)

(73) Assignee: Menicon Co., Ltd., Aichi (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/101,279
(22) PCT Filed: Nov. 10, 1997
(86) PCT No.: PCT/JP97/04076
    § 371 Date: Dec. 3, 1998
    § 102(e) Date: Dec. 3, 1998
(87) PCT Pub. No.: WO98/20813
    PCT Pub. Date: May 22, 1998

(30) Foreign Application Priority Data

Nov. 13, 1996 (JP) .............................. 8-301848

(51) Int. Cl.⁷ .................................................. A61F 2/14
(52) U.S. Cl. ..................................... 623/5.14; 623/5.15
(58) Field of Search ........................... 623/5.14, 5.15, 623/5.11, 5.13, 5.12, 5.16, FOR 104

(56) References Cited

U.S. PATENT DOCUMENTS

| | | | |
|---|---|---|---|
| 2,952,023 A | * 9/1960 | Rosen | 623/5.14 |
| 3,945,054 A | * 3/1976 | Fedorov et al. | 623/5.14 |
| 4,612,012 A | 9/1986 | White | |
| 4,772,283 A | * 9/1988 | White | 623/5.14 |
| 5,300,115 A | * 4/1994 | Py | 623/5.15 |

FOREIGN PATENT DOCUMENTS

| | | | |
|---|---|---|---|
| EP | 0333344 | 9/1989 | |
| EP | 0443094 | 8/1991 | |
| FR | 2649605 A | * 1/1991 | 623/FOR 104 |
| FR | 2687564 A | * 8/1993 | 623/FOR 104 |
| JP | 02-104364 | 4/1990 | |
| JP | 04-158859 | 6/1992 | |
| JP | 09-182762 | 7/1997 | |
| SU | 1124965 A | * 11/1984 | 623/FOR 104 |
| SU | 1660694 A1 | * 7/1991 | 623/FOR 104 |
| SU | 1734725 A | * 5/1992 | 623/FOR 104 |

* cited by examiner

Primary Examiner—David H. Willse
(74) Attorney, Agent, or Firm—Browdy and Neimark P.L.L.C.

(57) ABSTRACT

An artificial cornea comprising an optical element made of an optically transparent material, having a front surface and a posterior surface, and a skirt provided so as to support with surrounding at least a part of the optical element, characterized in that the skirt is provided with a flange on its side facing the interior of eyes during implantation of the artificial cornea and the flange radially protrudes outward from the skirt. The artificial cornea can be well compatible with ocular tissue, prevent leakage of intraocular aqueous humor and intraocular invasion of bacteria, reduce stimulation on palpebral conjunctiva and further, inhibit progression of the down growth, and which has no possibility of reduction in transparency of the optical element due to the down growth as well as detachment and extrusion from the implanted state.

18 Claims, 5 Drawing Sheets

ARTIFICIAL CORNEA

TECHNICAL FIELD

The present invention relates to an artificial cornea. More particularly, the present invention relates to an artificial cornea used for substituting a cornea of which function has been reduced or lost because of ocular tissue diseases or trauma therefore, thus recovering visual function.

BACKGROUND ART

An artificial cornea generally consists of an optical element made of a light-permeable material having good biocompatibility and a skirt for supporting the optical element by fixing on the surface of human ocular tissue or by insertion between the anterior layer and the posterior layer of the cornea. As such an artificial cornea, there are known an artificial cornea having an optical element and a skirt which are integrally molded from the same material, and an artificial cornea obtained by molding these optical element and skirt from different materials and combining them. As materials for such artificial corneas, there are mainly used polymethyl methacrylate, silicone and the like.

However, because biocompatibility of these materials with the surrounding ocular tissues is poor a slight gap is generated between an artificial cornea and the ocular tissue, and bacteria can invade into anterior chamber through the gap to cause suppurative endophthalmitis in some cases. In more severe cases, the implanted artificial cornea is rejected from the ocular tissue because of inflammation.

Recently, an artificial cornea of which a skirt is made of a material having a microporous structure has been approved. As an example of the artificial cornea of which the skirt is made of a material having a microporous structure, there is known an artificial cornea consisting of an optical element made of a visible light-permeable transparent plastic material and a skirt made of a flexible porous fluorocarbon polymer (Japanese Unexamined Patent Publication No. 158859/1992).

However, since such an artificial cornea has simply the skirt made of a flexible porous fluorocarbon polymer having the microporous structure, it is difficult to prevent leakage of aqueous humor and invasion of bacteria.

In addition, recently an artificial cornea has been proposed which has a skirt made of a hard material such as metal. However, this artificial cornea has such drawbacks that it is extremely difficult to suture the skirt with a suturing needle, that aqueous humor is lost to cause the operation to fail, and that because a metallic skirt is hard, poor in flexibility and shows high stress for the cornea, a part of the skirt is externally exposed by rupture of cornea within a short period of time after implantation into ocular tissue and bacteria can invade into the anterior chamber through the ruptured part to cause suppurative endophthalmitis. Further, such artificial cornea has such drawbacks that corneal tissue is necrosed resulting in extrusion of the artificial cornea, and that fixation is relaxed by an external force generated between the artificial cornea and eyelid resulting in extrusion of the artificial cornea.

In addition, among conventional artificial corneas, there are artificial corneas having a hole for a suture in the skirt in order to fix the artificial cornea. However, such artificial corneas have problems upon elevation of intraocular pressure, namely loss of aqueous humor and invasion of bacteria through the hole, and poor compatibility with the surrounding ocular tissue.

Then, the present inventors intensively studied to solve the above problems and achieved an artificial cornea by which problems such as compatibility with ocular tissue, leakage of intraocular aqueous humor, intraocular invasion of bacteria and stimulation on palpebral conjunctiva have been solved (Japanese Unexamined Patent Publication No. 182762/1997). As shown in FIG. 8, such an artificial cornea comprises an optical element 2 and a skirt 3 having a microporous structure, and a non-water-permeable layer 5 is provided on the surface thereof, so that invasion of bacteria from the external environment can be prevented and leakage of aqueous humor can be prevented. In addition, when the artificial cornea 10 is implanted, cells grow into the micropores of the skirt 3 from corneal tissue 6, resulting in firm binding between the artificial cornea 10 and the corneal tissue 6.

In this way, such an artificial cornea is an excellent one which has solved various conventional problems and has high availability. The present invention has been accomplished in order to further improve such an artificial cornea.

In the meanwhile, as shown in FIG. 9, cell growth occurs inherently at a wound such as an incisional wound and the wound subsequently heals. Upon this occurring, at a wounded part on cornea in contact with an artificial cornea, cells 11 grown from the corneal tissue 6 occasionally grow from the incisional wound surface facing the skirt 3 toward the posterior surface 12 of the artificial cornea 10 (side facing an anterior chamber). This phenomenon is referred to as "down growth". It is thought that this down growth is caused mainly because the restoring function of corneal epithelial cells at the incisional wound surface recognizes the artificial cornea 10 as a foreign body, so that the epithelial cells 11 do not migrate at the front surface 13 of the artificial cornea 10.

However, as the the time elapses after implantation, the down growth gradually progresses as shown in FIG. 9. Accordingly, it was found that, when the grown cells 11 initiate to cover the posterior surface of the optical element 2, not only is excellent transparency of the optical element 2 not fully maintained, but also the artificial cornea 10 is forwardly (extraocularlly) put and excluded from the corneal tissue 6 possibly resulting in extrusion of the artificial cornea even if the corneal tissue 6 and the artificial cornea 10 firmly adhere to each other due to the microporous structure in the skirt 3 as in the above invention.

The present invention has been accomplished in view of the above prior work, and aims at providing an artificial cornea which is well compatible with ocular tissue, which prevents leakage of intraocular aqueous humor and intraocular invasion of bacteria, reduces stimulation on palpebral conjunctiva and further inhibits progression of down growth, and which has no possibility of reduction in transparency of the optical element due to down growth as well as detachment and extrusion from the host cornea in the implanted state.

DISCLOSURE OF INVENTION

The present invention relates to an artificial cornea comprising an optical element made of an optically transparent material, having a front surface and a posterior surface, and a skirt provided so as to support with surrounding at least a part of the optical element, characterized in that the skirt is provided with a flange on its side facing the interior of eyes during implantation of the artificial cornea, and the flange radially protrudes outward from the skirt.

BEST MODE FOR CARRYING OUT THE INVENTION

Figure 1:
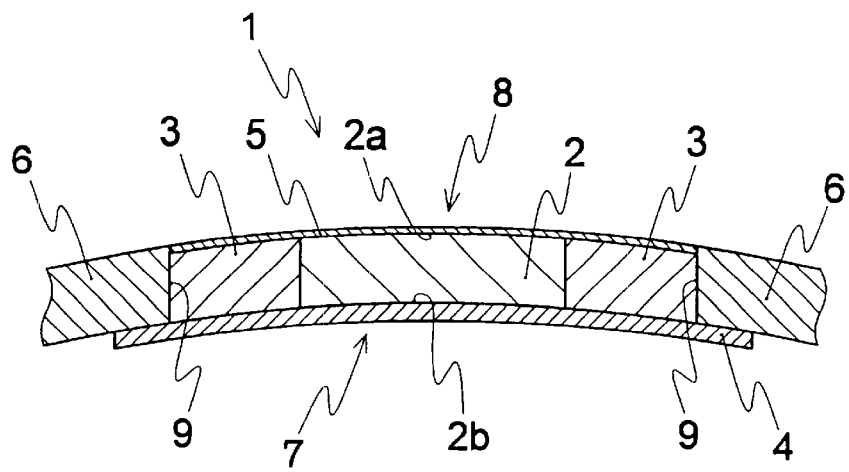
FIG. 1 is a schematic cross-sectional view showing one embodiment of an artificial cornea of the present invention, which is implanted into corneal tissue.

The artificial cornea of the present invention is an artificial cornea, as mentioned above, comprising an optical element made of an optically transparent material, having a front surface and a posterior surface, and a skirt provided so as to support with surrounding at least a part of the optical element, characterized in that the skirt is provided with a flange on its side facing the interior of eyes during implantation of the artificial cornea, and the flange radially protrudes outward from the skirt.

The optical element is positioned in the approximate center of the artificial cornea and exerts its visual function by its transparency.

Since the posterior surface of the artificial cornea is sometimes directly contacted with intraocular aqueous humor, the materials used for the optical element are preferably unharmful to the human body and excellent in safety. For instance, materials used for medical devices which are contacted with an organ or implanted into an organ such as contact lenses and intraocular lenses can be used. Examples of such materials are, for instance, polyurethane, silicone, acrylic resins represented by polymethyl methacrylate, polyesters represented by polyethylene terephthalate and the like. Among them, transparent ones are selected for use.

The planar shape of the optical element is the circular shape in order to keep an equable visual field.

The diameter of the optical element cannot be primarily determined because it differs depending upon the size of ocular tissue to be replaced with the artificial cornea and the like. The reasons are as follows. The external diameter of the skirt differs depending upon the diameter of tissue to be cut away from. Also, the width of the skirt sometimes suitably varies according to the ease of suturing through the skirt and the amount of cells growing into the skirt, so that the diameter of the optical element varies following variation of the width of the skirt. In view of the above factors and from the viewpoint of practicability, it is desired that the diameter of the optical element is usually 2 to 8 mm or so, preferably 3 to 6 mm or so.

It is desired that the thickness of the optical element is 0.05 to 1 mm or so from the viewpoint of mechanical strength. As regards the thickness, when refracting power is imparted thereto as may be necessary, the respective thicknesses of the central portion and that of the peripheral portion are made different. That is, at least a part of the optical element may be made into a spherical surface. In particular, when lens power is imparted to the optical element, spherical surfaces having different curvatures may be provided on the front surface and the posterior surface of the optical element, respectively.

Additionally, in the present invention, the skirt is made of a flexible material having a microporous structure.

The flexible material having a microporous structure has such advantage that suturing with ocular tissue is facilitated and adhesion with ocular tissue is enhanced. In addition, cells derived from the host cornea and blood capillaries grow into the micropores of the flexible material, so that the artificial cornea and ocular tissue firmly bind with good affinity to each other.

It is preferable that the flexible material having the microporous structure has such mechanical strength that the material is not torn by suturing, has a pore size into which cells derived from the surrounding ocular tissue can physically grow, coapts with ocular tissue to firmly adhere therewith and, additionally, is excellent in biocompatibility. For instance, materials used for medical devices which are contacted with an organ or implanted into an organ, such as contact lenses and intraocular lenses, can be used. Examples of such the materials are, for instance, spun-bounded non-woven fabrics made of materials such as polyurethane, silicone, collagen, polypropylene and polyester, and a sponge having an open cellular structure.

According to Jean T. Jacob-LaBarre et al, Progress in Biomedical Polymers, Plenum Press, New York, pages 27–39 (1990), the average pore size of micropores into which cells can grow is 10 to 100 $\mu$m. Therefore, the flexible porous materials used in the present invention suitably have a microstructure having approximately this range of pore size.

From the viewpoint that mechanical strength is retained and deformation by a force from intraocular pressure is prevented, in a case of usual keratplasty, a corneal graft is cut out with a circular trephine in many cases, the planar shape of the skirt is concentrically annular.

The inner diameter of the skirt is usually equal to the diameter of the optical element. In addition, although its external diameter cannot be primarily determined since it differs depending upon the size of ocular tissue to be substituted with the artificial cornea and the like, the external diameter is usually equal to the diameter of tissue to be cut away from or is larger than the diameter by 0.5 mm or so. For instance, it is desired that the external diameter is 6 to 20 mm or so, preferably 7 to 16 mm or so from the viewpoint of practicability.

In addition, the thickness of the skirt is not primarily determined, however, it is desired that the thickness is usually 0.01 to 3 mm or so, preferably 0.2 to 2.5 mm or so from the viewpoint of practicability. In particular, the thickness of the skirt is ideally approximately equal to the thickness of a host cornea.

In the present invention, it is preferable to impart curvature to the skirt so as to coincide with curvature of cornea.

When cells derived from ocular tissue grow into the micropores of the flexible material, the cells do not adhere well to some of the above flexible materials. Such flexible porous materials are hard to firmly combine with ocular tissue. Accordingly, when such the flexible porous materials are used, and in order to improve adherence of the cells thereto, the flexible porous materials are preferably previously subjected to surface modification such as plasma treatment modification. Also, it is preferable that the whole surface of the artificial cornea is subjected to surface modification. The surface modification of the flexible porous material refers to modification on the surface of the material which forms the microporous structure, for instance, the surface of fibers in a case of the non-woven fabric, or its interface in a case of the sponge having open cellular structure.

Furthermore, in the present invention it is preferable that a non-water-permeable layer is provided on a front surface of the skirt, or on a front surface of the skirt and a front surface of the optical element.

In the case that such a non-water-permeable layer is provided on a front surface of the skirt, or on a front surface of the skirt and a front surface of the optical element, there is an advantage achieved in that leakage of aqueous humor from the microinterstice of the skirt can be effectively prevented.

In addition, in the case wherein such a non-water-permeable layer is provided on a front surface of the skirt, or on a front surface of the skirt and a front surface of the optical element, there is an advantage achieved in that infection with bacteria can be effectively prevented, because intraocular invasion of bacteria from the outside through the micropores is inhibited.

Furthermore, in the case wherein such a non-water-permeable layer is provided on the surface (surface in contact with palpebral conjunctive) of the skirt, or on a front surface of the skirt and a front surface of the optical element, there is an advantage achieved in that stimulation due to friction with palpebral conjunctive, which is generated upon blinking can be remarkably reduced since the surface of the non-water-permeable layer is smooth.

In order to sufficiently exhibit these properties of the non-water-permeable layer, it is desired that the non-water-permeable layer shows substantial non-water absorptive property or lower water absorptive property of water content of at most 10%.

As the non-water-permeable materials, there can be used which are commonly used materials used for medical devices which are contacted with organs or implanted into organs, such as contact lenses and intraocular lenses. Examples of such materials are, for instance, polyurethane, silicone, acrylic resins represented by polymethyl methacrylate, polyesters represented by polyethylene terephthalate and the like. These resins may include fluorine atom in order to improve non-water-permeability.

Methods for forming the non-water-permeable layer at least on a front surface or in the interior of the skirt, or on a front surface of the skirt and a front surface of the optical element are not particularly limited. Examples of such methods are, for instance, (i) a method comprising preparing a non-water-permeable film as the non-water-permeable layer and adhering the non-water-permeable film to the front surface of the skirt, or on a front surface of the skirt and a front surface of the optical element, (ii) a method comprising contacting a front surface of the skirt with a solution obtained by dissolving a material used for the non-water-permeable layer in a suitable solvent, prior to complete evaporation of the solvent, and completely evaporating the solvent to form a non-water-permeable layer on a front surface of the skirt, or on a front surface of the skirt and a front surface of the optical element, (iii) a method comprising previously contacting a raw monomer of a material used for a non-water-permeable layer with a front surface of the skirt, or on a front surface of the skirt and a front surface of the optical element, applying a suitable energy such as heat or light thereto to polymerize the raw monomer and forming a non-water-permeable layer on a front surface of the skirt, or on a front surface of the skirt and a front surface of the optical element, and the like.

In addition, when the above method (iii) is employed, if a hydrophobic flexible material is used for the skirt and a hydrophobic raw monomer is used for the non-water-permeable layer, the hydrophobic raw monomer penetrates the micropores of the skirt to fill the interstices. As a result, ocular tissue is possibly prevented from growing into the skirt after implantation. Therefore, it is preferable that the flexible material is previously subjected to surface modification such as plasma treatment modification or that the raw monomer is instantaneously contacted therewith to be rapidly polymerized.

The thickness of the non-water-permeable layer cannot be primarily determined because it differs depending upon the kinds of the material composing the skirt. Usually, in order to impart sufficient non-water-permeability, prevent leakage of aqueous humor and invasion of bacteria, reduce stimulation on palpebral conjunctive, and keep flexibility of the skirt which is provided with the non-water-permeable layer, it is desired that the thickness is 0.005 to 0.5 mm or so, preferably 0.01 to 0.3 mm or so.

In order to effectively prevent leakage of aqueous humor and invasion of bacteria and reduce stimulation on palpebral conjunctiva, the non-water-permeable layer is preferably provided on the surface of the flexible material corresponding to the front surface of the resultant artificial cornea, particularly on the whole surface of the flexible material.

In addition, when the non-water-permeable layer is made of a soft material, suturing may be carried out by passing a suturing needle through the non-water-permeable layer. On the other hand, when the non-water-permeable layer is a relatively hard material, a suturing needle may not pass therethrough in some cases. Accordingly, it is desired that a microhole is provided on the non-water-permeable layer with such a degree that invasion of bacteria and leakage of aqueous humor do not occur. In addition, the microhole is preferably provided at such an angle that coincides with crook of the suturing needles.

Furthermore, in the artificial cornea of the present invention, a flange radially and annularly protrudes outwardly from the side of the optical element and protrudes outwardly and radially from the skirt so that the front surface of the flange contacts with a posterior surface of the skirt.

As described above, the artificial cornea of the present invention has great characteristics that the flange radially and annularly protrudes outwardly from the side of the optical element and protrudes outwardly and radially from the skirt.

In the artificial cornea of the present invention, the flange contacts with the posterior surface of the host cornea, caps an incised wound surface of the cornea to physically dam and inhibit down growth (growth of cells derived from corneal tissue toward the posterior surface of the artificial cornea). As a result, detachment and extrusion of the artificial cornea can be more assuredly inhibited, and transparency of the optical element is assuredly maintained without arrival of grown cells by down growth at the optical element.

Materials used for the flange are not particularly limited, and any materials may be used as long as they are unharmful to the human body and excellent in safety, and can attain the object of the present invention. For instance, the same materials as those used for the optical element, the skirt and the non-water-permeable layer may be used.

The flange radially protrudes outwardly from an end of the side of the skirt. In order to effectively exhibit effects of the present invention, the flange is formed so that it annularly and radially protrudes outwardly from an end of the side of the skirt over the whole periphery of the side of the artificial cornea facing the posterior surface of the host cornea during implantation of the artificial cornea.

In order to sufficiently exhibit effects of the present invention, such as maintenance of transparency of the optical element and prevention of extrusion of the artificial cornea, it is desired that the flange radially protrudes outwardly in the radial direction from the end of the side of the skirt by at least 0.5 mm. In order to easily insert the flange contacting with the posterior surface of the host cornea, it is desired that the flange protrudes from the skirt by at most 2 mm, usually by 1 mm or so.

In order to keep a sufficient distance between the artificial cornea or the host cornea and iris, and keep the volume of the anterior chamber, it is desired that the thickness of the flange (ocular optical axis direction) is at most 1 mm, preferably 0.1 to 0.5 mm.

In addition, from the viewpoint of strength, the flange is preferably made of such the- material and has such the thickness that it has strength endurable without extreme deformation even at a pressure of from normal intraocular pressure (20 mmHg or so) to a maximum of 50 mmHg. Therefore, from the viewpoint of strength, for instance, the thickness of the flange is preferably at least 0.1 mm.

Now, various embodiments of the artificial cornea of the present invention will be explained based on the following drawings.

FIG. 1 is a schematic cross-sectional view showing one embodiment of the artificial cornea of the present invention, which is implanted into corneal tissue.

In FIG. 1, the artificial cornea 1 of the present invention comprises the optical element 2 having the front surface 2a and the posterior surface 2b and the skirt 3. A planar shape of the skirt 3 is concentrically annular and the side of the inside diameter of the skirt 3 contacts with the side of the optical element 2. The skirt 3 is provided with the flange 4 which radially protrudes outwardly from the skirt 3 on its side (interior of anterior chambers) 7 which is configured to face the interior of the eye when the artificial cornea 1 is implanted into the corneal tissue 6. The flange 4 radially and annularly protrudes outwardly so that the front surface of the flange 4 contacts with the posterior surface of the skirt 3. The skirt 3 is further provided with the non-water-permeable layer 5 on the surface 8 thereof.

In this way, since the artificial cornea 1 of the present invention has the flange 4, the flange 4 caps the incised wound of cornea 9 from the side configured to face the aqueous chambers 7. Thereby, progression of down growth can be physically inhibited and, as a result, the posterior surface of the optical element 2 is not covered with the grown tissue by down growth and the transparency of the optical element 2 is assuredly maintained and, further, there is no possibility of detachment and extrusion of the implanted artificial cornea 1.

In the artificial cornea 1 shown in FIG. 1, the flange 4 is a separate member from the optical element 2 and the skirt 3 (that is, it is attached afterward). Also, the flange 4 is provided over the posterior surface of the optical element 2. In the present invention, the flange 4 may be integrally formed together with a part of the optical element 2 and/or the skirt 3, or may be separately formed, and thus there is no limitation in this regard.

Figure 2:
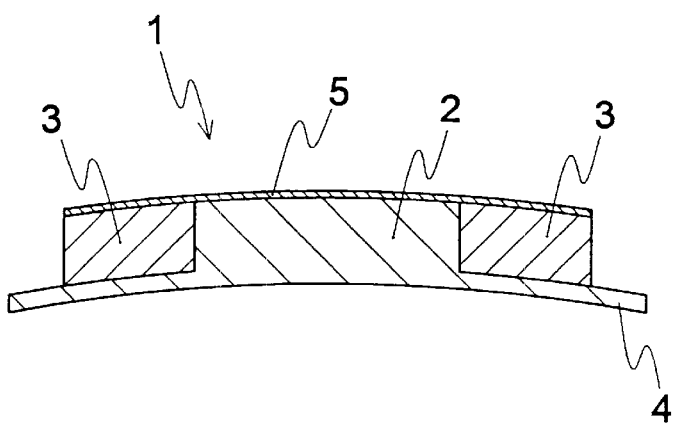
FIG. 2 is a schematic cross-sectional view showing one embodiment of an artificial cornea of the present invention

For instance, FIG. 2 is a schematic cross-sectional view showing one embodiment of the artificial cornea 1 of the present invention, comprising the optical element 2 and the skirt 3, wherein the flange 4 which is integrally formed together with the optical element 2 is provided so as to radially protrude outwardly from an end of the side of the skirt 3, and further, the skirt 3 and the optical element 2 are provided with the non-water-permeable layer 5 on the surface thereof.

Figure 3:
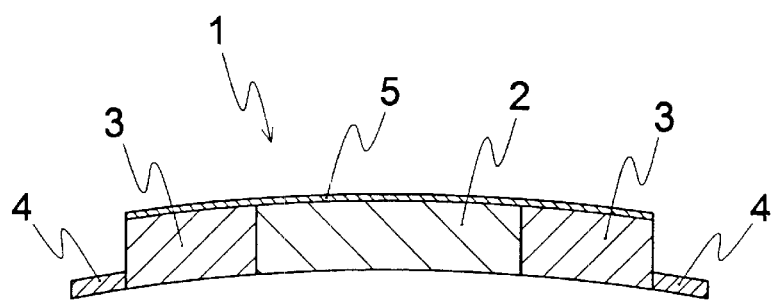
FIG. 3 is a schematic cross-sectional view showing one embodiment of an artificial cornea of the present invention.

FIG. 3 is a schematic cross-sectional view showing one embodiment of the artificial cornea 1 of the present invention, comprising the optical element 2 and the skirt 3, wherein the flange 4 is a separate member from the optical element 2 and the skirt 3, and is provided on the side surface of the skirt 3 so as to radially protrude outwardly from the lower end of the side surface of the skirt 3, and further the skirt 3 and the optical element 2 are provided with the non-water-permeable layer 5 on the surface thereof.

Figure 4:
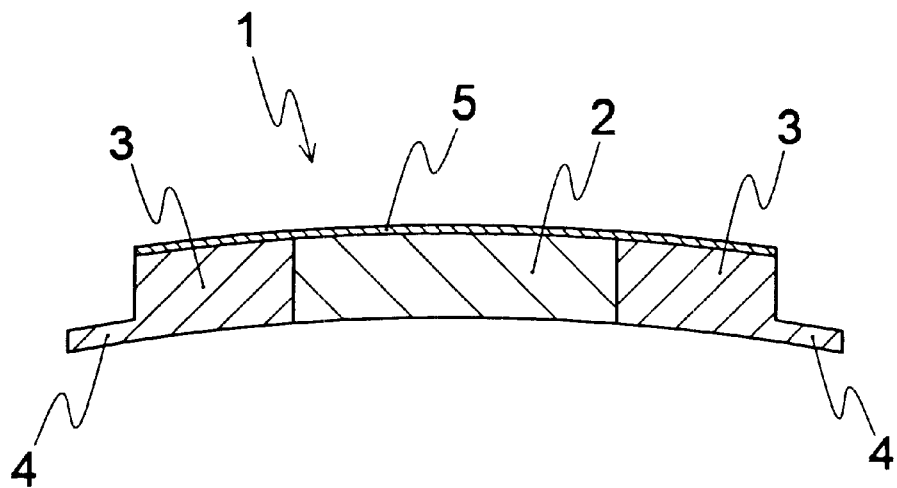
FIG. 4 is a schematic cross-sectional view showing one embodiment of an artificial cornea of the present invention.

FIG. 4 is a schematic cross-sectional view showing one embodiment of the artificial cornea 1 of the present invention, comprising the optical element 2 and the skirt 3, wherein the flange 4, which is integrally formed together with the skirt 3 is provided so as to radially protrude outwardly from the skirt 3, and further the skirt 3 and the optical element 2 are provided with the non-water-permeable layer 5 on the surface thereof.

Figure 5:
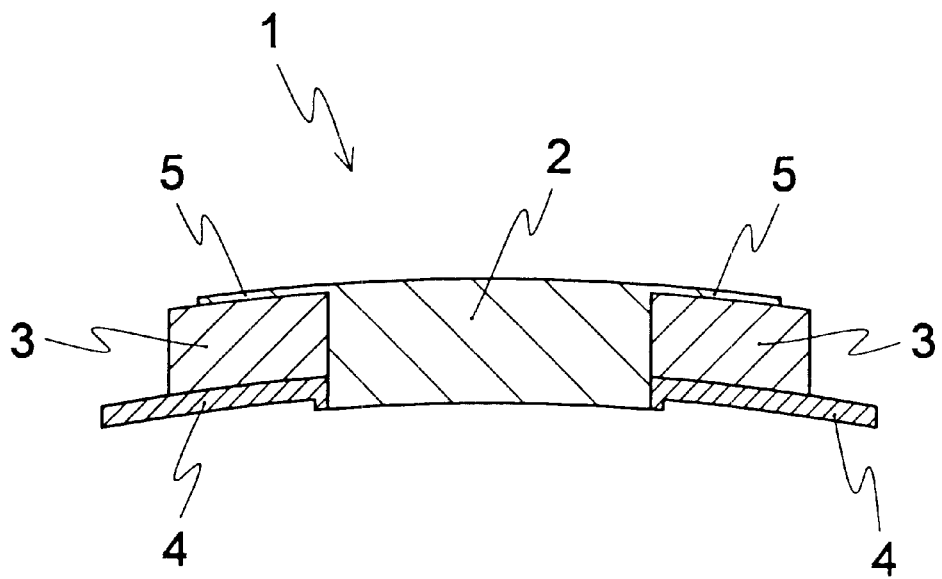
FIG. 5 is a schematic cross-sectional view showing one embodiment of an artificial cornea of the present invention.

FIG. 5 is a schematic cross-sectional view showing one embodiment of the artificial cornea 1 of the present invention, comprising the optical element 2 and the skirt 3, wherein the non-water-permeable layer 5, which is integrally formed together with the optical element 2, is provided on the surface of the skirt 3, and the annular flange 4 having an opening of a size approximately equal to the diameter of the optical element 2 in a central portion thereof is provided so as to radially protrude outwardly from an end of the side of the skirt 3, and further a part of the bottom of the optical element 2 passes through the opening of the flange 4.

In the meanwhile, curvature is imparted to each artificial cornea 1 shown in schematic cross-sectional views of FIGS. 1 to 5. The artificial cornea of the present invention is not limited by whether curvature is imparted or not.

A method for producing the artificial cornea of the present invention is not particularly limited and various methods can be utilized.

The artificial cornea 1 shown in FIG. 1 can be obtained, for instance, by separately preparing the optical element 2, the skirt 3, the flange 4 and the non-water-permeable layer 5, and appropriately bonding them using an adhesive or the like. For instance, molded articles (e.g. sheets) obtained by injection molding, compression molding, roll molding, casting from a solution or the like may be used for the optical element 2 and the non-water-permeable layer 5. In addition, for instance, non-woven fabric, sponge and the like may be used for the skirt 3, as mentioned above. When the adhesive is used upon the above bonding, it is necessary not to deteriorate transparency of the optical element 2.

In addition, the artificial cornea 1 shown in FIG. 2 can be obtained, for instance, by integrally molding the optical element 2 and the flange 4 and appropriately bonding this optical element 2 with the skirt 3 and the non-water-permeable layer 5 using an adhesive or the like. Integral molding of the optical element 2 and the flange 4 can be easily carried out using a mold having the desired shape, for instance, by injection molding, compression molding or the like. In addition, a process for producing the skirt 3 and the non-water-permeable layer 5, and a process for bonding these materials, may be the same as those described for the artificial cornea 1 shown in FIG. 1.

The thus obtained artificial cornea of the present invention having the above essential components is well adapted to cooperate with ocular tissue, to prevent leakage of intraocular aqueous humor and invasion of bacteria, and at the same time to reduce stimulation on palpebral conjunctive. Furthermore, the artificial cornea is well adapted to inhibit progression of down growth, so that there is no possibility of reduction in transparency of the optical element due to down growth as well as detachment and extrusion from the implanted state.

In the present invention, in order to enhance compatibility of the artificial cornea with tears and aqueous humor and impart at least good optical property thereto, it is desired that a portion of the artificial cornea which contacts with tears and aqueous humor, preferably the whole surface of the artificial cornea, be subjected to surface modification.

A method for carrying out surface modification to the artificial cornea of the present invention is not particularly limited. Examples of the method are, for instance, a method comprising graft bonding (polymerizing) a hydrophilic component (monomer) such as acrylamide or hydroxyethyl methacrylate with the surface of the artificial cornea, a corona discharge treatment method, a plasma treatment method, a method comprising immersing the artificial cornea in a solution obtained by dissolving a hydrophilic polymer such as collagen in a suitable solvent and carrying out modification with crosslinking it by irradiation with light, and the like.

Next, the artificial cornea of the present invention will be more specifically explained on the basis of Examples. However, the scope of the present invention is not limited to only the Examples.

EXAMPLE 1

Figure 6:
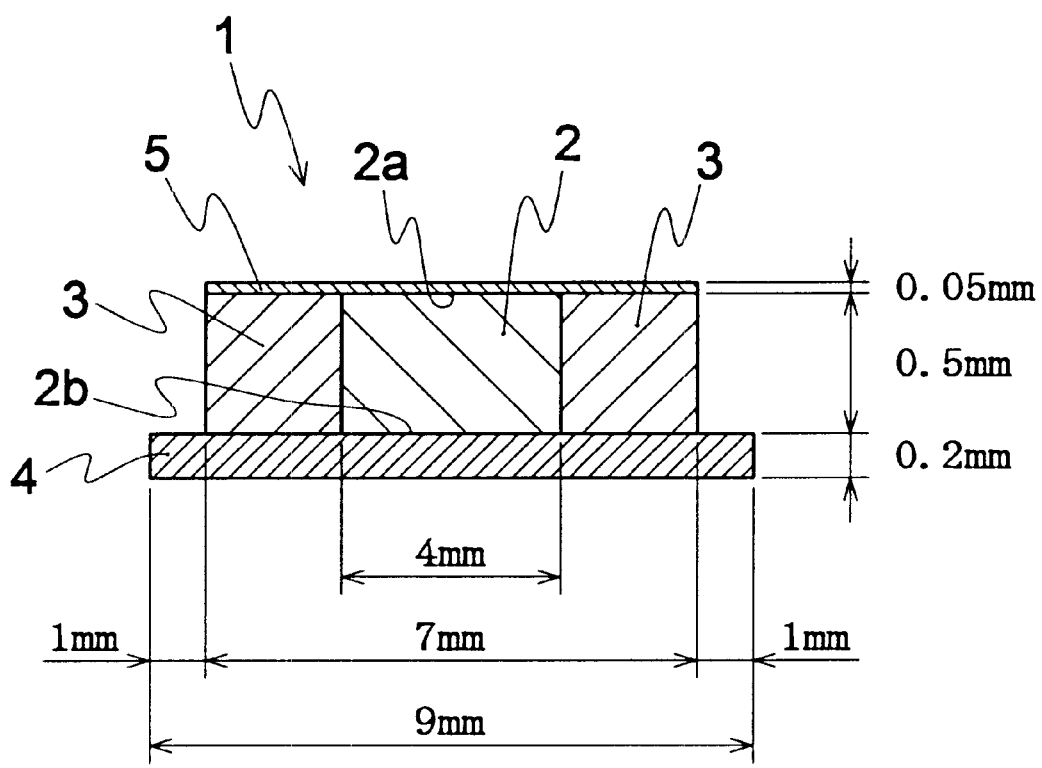
FIG. 6 is a schematic cross-sectional view showing the artificial cornea of the present invention obtained in Example 1.

An artificial cornea 1 having the shape shown in FIG. 1 (dimension is shown in FIG. 6) was produced.
(1) Production of a Transparent Optical Element 2

A transparent polyetherpolyurethane sheet having a thickness of 0.5 mm was cut out with trephine to provide a diameter of 4 mm.
(2) Production of a Skirt 3

Non-woven fabric having a thickness of 0.5 mm (METSUKE (Japanese Industrial Standard): 50 g/m$^2$), made of polyetherpolyurethane was cut out into ring-donut-parts having an external diameter of 7 mm and an inner diameter of 4 mm with a trephine.
(3) Production of a Non-water-permeable Layer 5, and Bonding of the Non-water-permeable Layer 5 to the Optical Element 2 and the Skirt 3

Adhesion of the optical element 2 and the skirt 3 to a polyether polyurethane sheet (the same material as that of the non-water-permeable layer 5 and the optical element 2) having a thickness of 0.05 mm, obtained by a casting method, was carried out using a tetrahydrofuran solution of the same polyether polyurethane as an adhesive, so that the front surface 2a of the optical element 2 was bonded to the non-water-permeable layer 5. The cast solution was fully dried and then concentrically annularly cut out along an external diameter of the skirt 3 with a trephine to provide a diameter of 7 mm.
(4) Production of a Flange 4, and Bonding of the Flange 4 to the Optical Element 2, the skirt 3 and the Non-water-permeable Layer 5:

Adhesion of the parts obtained in item (3) to a polyether polyurethane sheet (the same material as that of the flange 4 and the optical element 2) having a thickness of 0.2 mm, obtained by a casting method, was carried out using the same adhesive used in item (3), so that the posterior surface 2b of the optical element 2 was bonded to the flange 4. The cast solution was fully dried and then concentrically annularly cut out with a trephine to provide a diameter of 9 mm so that the flange 4 protruded radially from an end of the side of the skirt 3 by 1 mm.

The thus obtained artificial cornea was sterilized with ethylene oxide gas and implanted into the eye of a rabbit, and it was found that suturing could be easily carried out. Thereafter, the state was observed with the passage of time. As a result, it was found that, even after 26 weeks elapsed from implantation, there was no extrusion and detachment of the artificial cornea, the artificial cornea firmly coapted with ocular tissue, transparency of the optical element of the artificial cornea was retained, and leakage of intraocular aqueous humor and inflammation such as intraocular infection were not recognized. Thus, the good state was maintained.

EXAMPLE 2

Figure 7:
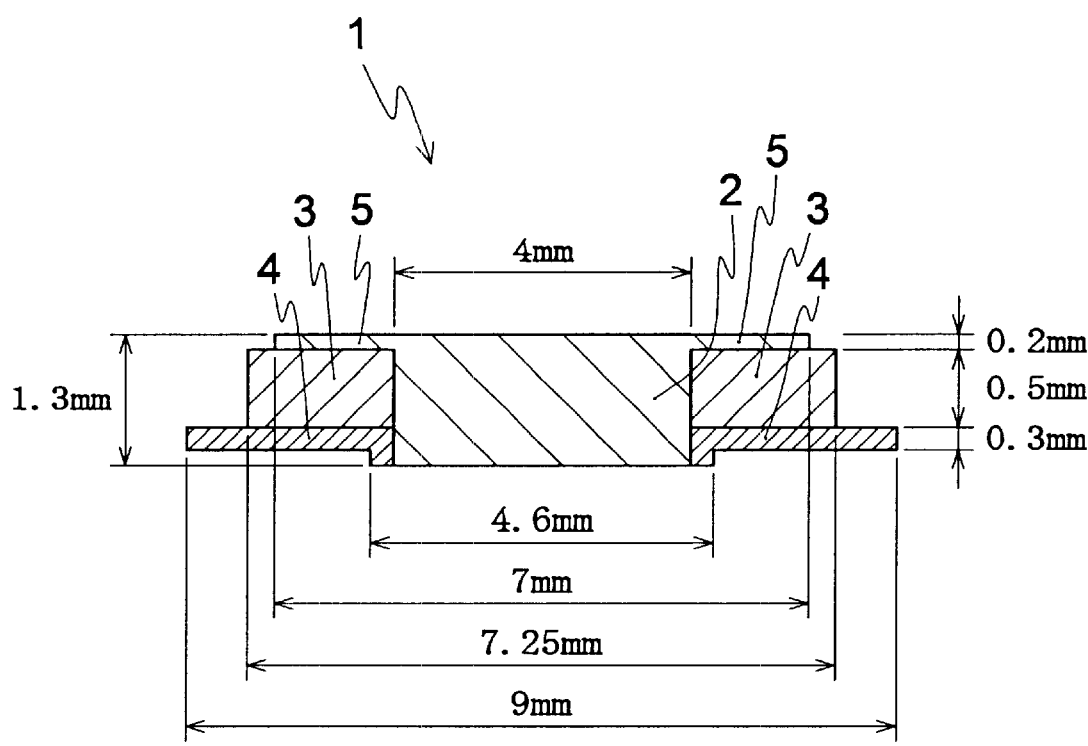
FIG. 7 is a schematic cross-sectional view showing the artificial cornea of the present invention obtained in Example 2.
Figure 8:
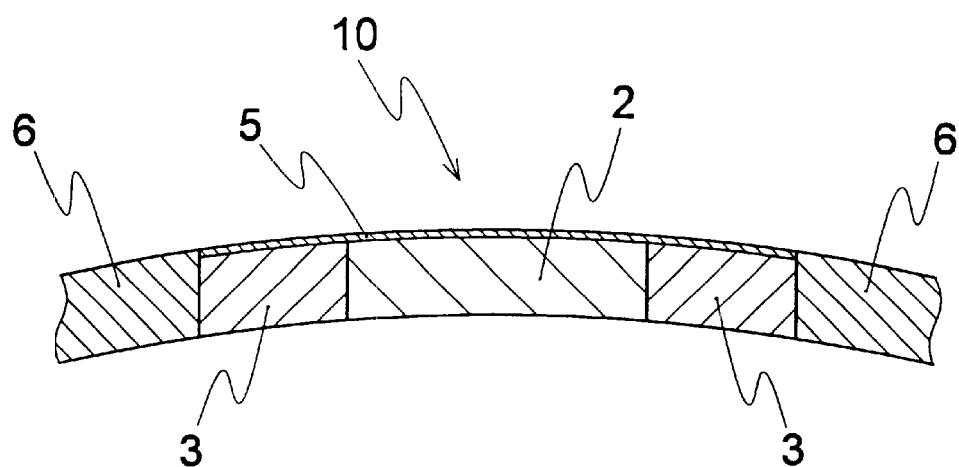
FIG. 8 is a schematic cross-sectional view showing one embodiment of an earlier artificial cornea which is implanted into corneal tissue.
Figure 9:
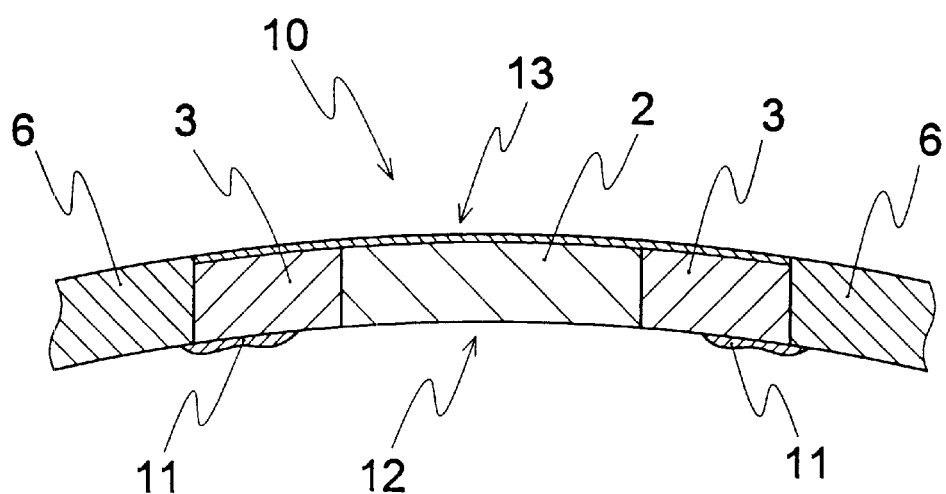
FIG. 9 is a schematic cross-sectional view showing one embodiment of an earlier artificial cornea which is implanted into corneal tissue.

An artificial cornea 1 having the similar shape shown in FIG. 5 (dimension is shown in FIG. 7) was produced.
(1) Production of a Transparent Optical Element 2 and a Non-water-permeable Layer 5

A piece having a diameter of 10 mm and a thickness of 5 mm, made of polyethylene terephthalate was subjected to cutting and polishing process to give parts in which the transparent optical element 2 having a diameter of 4 mm and a thickness of 1.3 mm, made of polyethylene terephthalate and the non-water-permeable layer 5 having a diameter of 7 mm and a thickness of 0.2 mm, made of polyethylene terephthalate were integrally formed.

Furthermore, in order to easily suture, microholes for suturing having a diameter of 0.4 mm were appropriately provided at eight positions on the non-water-permeable layer 5 away from the optical element 2 (not shown in Figure).
(2) Production of a Skirt 3

Polyethylene terephthalate fabric having a thickness of 0.5 mm was cut out with a trephine into ring-donut-parts having an external diameter of 7.25 mm and an inner diameter of 4 mm.

In the same manner as in the production of the optical element 2 and the non-water-permeable layer 5, a piece made of polyethylene terephthalate was subjected to cutting and polishing process to give ring-donut-parts having a thickness (of the flange 4) of 0.3 mm, an external diameter of 9 mm and an inner diameter of 4 mm.
(4) Bonding of the Optical Element 2 and the Non-water-permeable Layer 5 to the Skirt 3 and the flange 4.

The central opening of the ring-donut-skirt 3 obtained in the item (2) was put in the optical element 2 along its external circuit in the parts in which the optical element 2 and the non-water-permeable layer 5 were integrally formed, obtained in the item (1). Next, the central opening of the ring-donut-flange 4 obtained in the item (3) was put in the optical element 2 along its external circuit from a direction which the central opening of the skirt 3 was put therein. Moreover, a part of the optical element 2 (thickness: 0.3 mm) protruded from the central opening of the flange 4. Then, the positions where the flange 4 was put in the optical element 2 were welded together with by heating.

The thus obtained artificial cornea was sterilized with ethylene oxide gas and implanted into the eye of a rabbit and it was found that suturing could be easily carried out through the above microholes for suturing. Thereafter, the state was observed with the passage of time. As a result, it was found that, even after 13 weeks elapsed from implantation, there was no extrusion and detachment of the artificial cornea, the artificial cornea firmly coapted with ocular tissue, transparency of the optical element of the artificial cornea was retained, and leakage of intraocular aqueous humor and inflammation such as intraocular infection were not recognized. Thus, the good state was maintained.

Industrial Applicability

Since the artificial cornea of the present invention can be easily sutured to ocular tissue and easily fixed to ocular tissue, it well coadapts with ocular tissue, can prevent leakage of intraocular aqueous humor and invasion of bacteria and can reduce stimulation on palpebral conjunctive. Furthermore, the artificial cornea can inhibit progression of down growth, so that there is no possibility of reduction in transparency of the optical element due to down growth as well as detachment and extrusion from the implanted site.

What is claimed is:

1. An artificial cornea comprising
   (1) an optical element which is made of an optically transparent material, and a planar shape of which is circular, having a front surface, a posterior surface and a side face;
   (2) a skirt having a microporous structure into which corneal tissue grows, and a planar shape of which is concentrically annular, surrounding a part of the side face or the whole side face of said optical element; and
   (3) a flange radially and annularly protruding outwardly from the side face of said optical element so that a front surface of said flange contacts with a posterior surface of said skirt;
   wherein the average pore size of micropores in said skirt is 10 to 100 μm, and the micropores are open cells;
   wherein thickness of said skirt is the same as that of an incisional wound surface of a cornea so that a side face of said skirt is configured to contact with the whole incisional wound surface;
   wherein said flange protrudes outwardly to radius direction from said skirt by 0.5 to 2 mm; and
   wherein parts of said flange protruding from an end of the side face of said skirt are configured to contact with the inside of the cornea during implantation of the artificial cornea into the corneal tissue so that the artificial cornea is not excluded from the ocular tissue.

2. The artificial cornea of claim 1, wherein said flange has a thickness of 0.1 to 0.5 mm.

3. The artificial cornea of claim 1, where a non-water-permeable layer is provided on a front surface of said skirt, said non-water-permeable layer effecting prevention of infection with bacteria.

4. The artificial cornea of claim 3, wherein the non-permeable layer shows non-water absorptive property or lower water absorptive property with water content of at most 10%.

5. The artificial cornea of claim 1, wherein the whole surface of the artificial cornea is subjected to surface modification.

6. The artificial cornea of claim 5, wherein the surface modification comprises a plasma treatment modification.

7. The artificial cornea of claim 1, wherein at least one of the front surface and the posterior surface of said optical element has a spherical surface.

8. The artificial cornea of claim 1, wherein lens power is imparted to said optical element.

9. The artificial cornea of claim 1, wherein said optical element has spherical surfaces having different curvatures on the front surface and the posterior surface, respectively.

10. An artificial cornea comprising
    (1) an optical element which is made of an optically transparent material, and a planar shape of which is circular, having a front surface, a posterior surface and a side face;
    (2) a skirt having a microporous structure into which corneal tissue grows, and a planar shape of which is concentrically annular, surrounding a part of the side face or the whole side face of said optical element; and
    (3) a flange radially and annularly protruding outwardly from the side face of said optical element so that a front surface of said flange contacts with a posterior surface of said skirt;
    wherein the average pore size of micropores in said skirt is 10 to 100 μm, and the micropores are open cells;
    wherein thickness of said skirt is the same as that of an incisional wound surface of a cornea so that a side face of said skirt is configured to contact with the whole incisional wound surface; and
    wherein said flange protruding from an end of the side face of said skirt is configured to contact with the inside of the cornea during implantation of the artificial cornea into the corneal tissue so that the artificial cornea is not excluded from the ocular tissue.

11. The artificial cornea of claim 10, wherein said flange has a thickness of 0.1 to 0.5 mm.

12. The artificial cornea of claim 10, wherein a non-water-permeable layer is provided on a front surface of said skirt, or on both front surfaces of said skirt and said optical element, said non-water-permeable layer effecting prevention of infection with bacteria.

13. The artificial cornea of claim 12, wherein the non-water-permeable layer shows non-water absorptive property or lower water absorptive property with water content of at most 10%.

14. The artificial cornea of claim 10, wherein a part of a surface or the whole surface of the artificial cornea is subjected to surface modification.

15. The artificial cornea of claim 14, wherein the surface modification comprises a plasma treatment modification.

16. The artificial cornea of claim 10, wherein at least a part of the front surface and the posterior surface of said optical element has a spherical surface.

17. The artificial cornea of claim 10, wherein lens power is imparted to said optical element.

18. The artificial cornea of claim 10, wherein said optical element has spherical surfaces having different curvatures on the front surface and the posterior surface, respectively.

* * * * *